United States Patent [19]
Jakobson et al.

[11] Patent Number: 5,466,719
[45] Date of Patent: Nov. 14, 1995

[54] POLYGLYCEROL FATTY ACID ESTER MIXTURE

[75] Inventors: Gerald Jakobson; Werner Siemanowski, both of Rheinberg; Karl-Heinz Uhlig, Krefeld-Traar, all of Germany

[73] Assignee: Solvay Fluor und Derivate GmbH, Hanover, Germany

[21] Appl. No.: 101,075

[22] Filed: Aug. 4, 1993

[30] Foreign Application Priority Data

Aug. 7, 1992 [DE] Germany .............. 42 26 174.0

[51] Int. Cl.[6] .................................... A61K 31/23
[52] U.S. Cl. ................ 514/785; 514/786; 554/172; 554/173; 554/227
[58] Field of Search ................... 514/785, 786; 554/172, 173, 227

[56] References Cited

U.S. PATENT DOCUMENTS

| | | | |
|---|---|---|---|
| 5,147,644 | 9/1992 | Oppenlaender et al. | 424/401 |
| 5,247,114 | 9/1993 | Jakobson et al. | 554/227 |

FOREIGN PATENT DOCUMENTS

| | | |
|---|---|---|
| 299295 | 1/1989 | European Pat. Off. . |
| 499700 | 8/1992 | European Pat. Off. . |
| 3721003 | 12/1988 | Germany . |
| 4105305 | 8/1991 | Germany . |
| 4023593 | 1/1992 | Germany . |
| 3410520 | 12/1992 | Germany . |

*Primary Examiner*—Richard L. Raymond
*Attorney, Agent, or Firm*—Evenson, McKeown, Edwards & Lenahan

[57] ABSTRACT

Polyglycerol fatty acid ester mixtures of mono- di- and polyesters of polyglycerols having a degree of polymerization of 2 to 8 and at least one saturated and/or unsaturated fatty acid, the mixtures having an HLB of greater than 8 and containing 0 to less than 5 wt-% diglycerol fatty acid esters, 20 to 65 wt-% triglycerol fatty acid esters, 20 to 50 wt-% tetraglycerol fatty acid esters and 5 to 40 wt-% higher polyglycerol fatty acid esters, in which the fatty acid component consists of one or more fatty acids selected from the saturated and/or unsaturated, branched and/or unbranched $C_6$- to $C_{14}$-fatty acids containing less than 10 wt-% fatty acids having more than 14 carbon atoms; bath additive preparations containing such polyglycerol fatty acid ester mixtures; methods of using such polyglycerol fatty acid ester mixtures, and a process for preparing such mixtures.

42 Claims, No Drawings

POLYGLYCEROL FATTY ACID ESTER MIXTURE

BACKGROUND OF THE INVENTION

The present invention relates to a polyglycerol fatty acid ester mixture of mono-, di- and polyesters of polyglycerols having a degree of polymerization of 2 to 8 and at least one saturated and/or unsaturated fatty acid; to a bath additive composition containing this polyglycerol fatty acid ester mixture; to the use of the polyglycerol fatty acid ester mixture, and to a process for preparing the polyglycerol fatty acid ester mixture.

It is already known to employ polyglycerol fatty acid esters and ester mixtures as surface-active compounds for the preparation and stabilization of oil/water and water/oil systems because of their lipophilic and hydrophilic properties. These polyglycerol fatty acid esters are non-defined partial esters of polyglycerols with saturated and/or unsaturated fatty acids, there being numerous possibilities for the preparation of emulsifiers and solubilizers having suitably balanced fat and water solubility. The HLB of polyglycerol fatty acid esters or ester mixtures depends on their composition. This is determined by the synthesis route, in particular by the type and ratio of the reactants and by the reaction conditions.

The preparation of surface-active compounds having very specific HLBs by esterification of polyglycerol with fatty acids, however, poses various problems.

On the one hand, the reaction mechanisms with respect to the selectivity of the esterification and the number of substitutions occurring on the polyglycerol basic skeleton are to date largely unknown, so the activity of the polyglycerol fatty acid esters as emulsifiers and solubilizers can neither be checked nor clearly predicted.

It is particularly difficult, therefore, to prepare products having very specific surface-active properties by esterification of mixtures of various glycerol oligomers with fatty acids, especially as mixtures of this type, due to the industrial processes for their preparation, frequently consist of a large number of different polyglycerols and a relatively greater or lesser amount of cyclic glycerol oligomers.

On the other hand, the hydrophilic and lipophilic properties of the polyglycerol fatty acid esters are determined by the esterified fatty acids, the polyglycerol basic skeleton and the degree of esterification. In this connection, the increasing hydrophilicity of the polyglycerols with increasing degree of polymerization, the specific surface activity of the fatty acids and fatty acid mixtures selected in each case as the esterification product, their solubility in the polyglycerol and the unusually high decrease in the HLB of the polyglycerol fatty acid esters or ester mixtures when using fatty acids having high molecular weights are particularly to be taken into account. Additionally, the esterification ratio is dependent on the Weight or molar ratios of the reactants employed, polyglycerol and fatty acid, to one another.

In the prior art, polyglycerol fatty acid esters having defined properties have been prepared until now by esterification under controlled conditions of very specific glycerol oligomers, such as, for example, triglycerol or tetraglycerol, preferably with the use of protective groups.

The use of polyglycerol mixtures as the esterification starting material is known, for example, from published German Patent Application No. DE 4,023,593. This document describes esterification of a polyglycerol mixture which not only has a wide distribution with respect to the glycerol oligomers contained in it, but which also, due to the process by which it is prepared, contains a relatively greater or lesser amount of cyclic polyglycerols. The esterification product according to published German Patent Application No. DE 4,023,593 is a non-liquid surfactant whose action as an oil-in-water emulsifier is unsatisfactory, particularly with respect to the HLB (hydrophilic-lipophilic balance) achieved and the stability of the emulsions prepared.

Ethereal, mineral and also fatty animal and vegetable oils are very difficult to emulsify and/or solubilize, and there is a need for emulsifiers and/or solubilizers Which can effectively emulsify and/or solubilize these oils. Past attempts to use polyglycerol fatty acid esters or ester mixtures to emulsify or solubilize such oils have yielded only unsatisfactory results.

SUMMARY OF THE INVENTION

It is the object of the present invention to provide a polyglycerol fatty acid ester mixture which is a water-soluble liquid and is useful as an emulsifier for preparing stable oil-in-water systems.

Another object of the invention is to provide a polyglycerol fatty acid ester mixture in which the polyglycerol component contains a narrow distribution of glycerol oligomers and little or no cyclic components.

A further object of the invention is to provide a polyglycerol fatty acid ester mixture which is suitable for emulsifying and/or solubilizing ethereal, mineral and/or fatty animal and vegetable oils, which are normally difficult to emulsify or solubilize.

Additionally it is an object of the invention to provide a polyglycerol fatty acid ester mixture which has a high hydrophilicity.

It is also an object of the invention to provide a polyglycerol fatty acid ester mixture which has advantageous dermatological and toxicological properties so that it can be used provide skin-care effects in cosmetic and/or pharmaceutical preparations.

These and other objects of the invention are achieved by providing a polyglycerol fatty acid ester mixture of mono-, di- and polyesters of a polyglycerol having a degree of polymerization of 2 to 8 and at least one fatty acid selected from the group consisting of saturated and unsaturated, branched and unbranched $C_6$- to $C_{14}$-fatty acids containing less than 10 wt-% of fatty acids having more than 14 carbon atoms, wherein said polyglycerol fatty acid ester mixture has an HLB of greater than 8 and contains 0 to 5 parts by weight diglycerol fatty acid esters, 20 to 65 parts by weight triglycerol fatty acid esters, 20 to 50 parts by weight tetraglycerol fatty acid esters, and 5 to 40 parts by weight higher polyglycerol fatty acid esters, in a total of 100 parts by weight of said ester mixture.

In accordance with a further aspect of the invention, the objects are also achieved by providing a process for preparing a polyglycerol fatty acid ester mixture of mono-, di- and polyesters of polyglycerols having a degree of polymerization of 2 to 8 and at least one saturated and/or unsaturated fatty acid, said process comprising the steps of initially heating a reaction mixture comprising a polyglycerol containing 0 to 5 wt-% diglycerol, 20 to 65 wt-% triglycerol, 20 to 50 wt-% tetraglycerol, and 5 to 40 wt-% higher polyglycerols, and at least one fatty acid selected from the group consisting of saturated and unsaturated, branched and unbranched $C_6$- to $C_{14}$-fatty acids containing less than 10 wt-% fatty acids having more than 14 carbon atoms, in a molar ratio of polyglycerol to fatty acid of 4:1 to 1:1 and in the presence of at least one catalyst, to a temperature of at least 140° C. and reducing the pressure to at most 600 mbar;

subsequently heating the reaction mixture in a temperature range from 140° to 220° C. under control of a temperature program, and simultaneously reducing the pressure under control of a pressure program from 600 to 10 mbar;

removing resulting water of reaction by continuous distillation, and upon attaining an acid number of less than 3, cooling the resulting polyglycerol fatty acid ester mixture.

DETAILED DESCRIPTION OF PREFERRED EMBODIMENTS

It has now been found that a polyglycerol fatty acid ester mixture containing:

0 to 5 parts by weight diglycerol fatty acid esters, 20 to 65 parts by weight triglycerol fatty acid esters, 20 to 50 parts by weight tetraglycerol fatty acid esters, and 5 to 40 parts by weight higher polyglycerol fatty acid esters for a total of 100 parts by weight, in which the fatty acid component consists of one or more fatty acids selected from the saturated and/or unsaturated, branched and/or unbranched $C_6$- to $C_{14}$-fatty acids containing less than 10 wt-% of fatty acids having more than 14 carbon atoms, and the HLB of the polyglycerol fatty acid ester mixture is greater than 8, has all the advantageous properties required to achieve the objects of the invention.

It has furthermore been found that the liquid polyglycerol fatty acid ester mixture according to the invention is not only outstandingly suitable for the emulsification and solubilization of oils and oily compounds or compositions, in particular ethereal and fatty vegetable or animal oils, but surprisingly also causes a spontaneous emulsification of the aforementioned oils, in particular even in dilute aqueous solutions. The mixing of these oils with the polyglycerol fatty acid ester mixture according to the invention results in optically clear liquids, since the oily compound is solubilized to a great extent.

On the basis of its high hydrophilicity, the polyglycerol fatty acid ester mixture according to the invention can be used as a solvent and emulsifier, solubilizer, wetting agent and dispersing agent for the preparation of stable oil/water systems. Products, in particular cosmetic and pharmaceutical preparations which contain the polyglycerol fatty acid ester mixture according to the invention as a surfactant, are indefinitely stable at the customary test temperatures and thus cause no storage and transport problems. Small concentrations of acid or salt also cannot disturb the established phase equilibrium: for example no turbidity or precipitates occur in a mixture of 1 part by weight of the polyglycerol fatty acid ester mixture according to the invention and 100 parts by weight of a 10% strength by weight sodium chloride solution. The polyglycerol fatty acid ester mixture according to the invention is therefore combinable with a large number of substances and can find a wide range of application.

Compared with the ethoxylates frequently employed as emulsifiers, solubilizing agents and wetting agents, the polyglycerol fatty acid ester mixture according to the invention has a better biodegradability and can additionally be incorporated into cosmetic and pharmaceutical preparations and foodstuffs without problems on account of its advantageous toxicological and dermatological properties.

The polyglycerol fatty acid ester mixture according to the invention moreover has a high skin-care action and in particular a high oil-restoring capacity.

According to a preferred embodiment, the polyglycerol fatty acid ester mixture according to the invention contains:

0 to 3 parts by weight diglycerol fatty acid esters, 22 to 32 parts by weight triglycerol fatty acid esters, 39 to 49 parts by weight tetraglycerol fatty acid esters, and 24 to 34 parts by weight higher polyglycerol fatty acid esters, for a total of 100 parts by weight, in which the fatty acid component consists of one or more fatty acids selected from the saturated and/or unsaturated, branched and/or unbranched $C_8$- to $C_{12}$-fatty acids containing less than 5 wt-% of fatty acids having more than 14 carbon atoms, and in which the HLB of the polyglycerol fatty acid ester mixture is greater than 10.

According to a preferred embodiment, the polyglycerol fatty acid ester mixture according to the invention contains 5 to 20 percent by weight of pentaglycerol fatty acid esters.

As used herein the term "higher polyglycerol fatty acid esters" refers to derivatives of glycerol oligomers which have 5 to 8 glycerol units in the molecule, i.e. which have a degree of polymerization of 5 to 8.

Suitable fatty acids in the polyglycerol fatty acid ester mixture according to the invention include all saturated and unsaturated, branched and unbranched $C_6$- to $C_{14}$-fatty acids, individually or in mixtures with one another. It has been found that the lower limit in the carbon atom number is fixed by that fatty acid which, with the shortest chain, just still shows surface activity as the esterification product. Since fatty acids having $C_{15}$ and higher carbon chains dissolve poorly in polyglycerol, the upper limit of the fatty acids selected according to the invention is fixed by those having a maximum carbon atom number of about 14.

However, it has been shown that low contents of fatty acids having $C_{15}$ and higher carbon chains do not interfere with the particular surface-active properties of the polyglycerol fatty acid ester mixture according to the invention, which is why the fatty acids selected according to the invention can have a content of less than 10 per cent by weight, preferably less than 5 per cent by weight, of fatty acids having more than 14 carbon atoms, it also being possible by this means to incorporate certain additional properties in the polyglycerol fatty acid ester mixture according to the invention.

Preferably, the fatty acid component consists of caprylic acid, capric acid, lauric acid, undecenoic acid, 2-ethylhexanoic acid and/or coconut fatty acid. In particular, these fatty acids are used to incorporate certain additional properties, such as skin-care or antimycotic actions, in the polyglycerol fatty acid ester mixture according to the invention.

Particularly advantageous properties with respect to caring action and surface activity are furthermore achieved if the polyglycerol fatty acid ester mixture according to the invention consists to more than 50 per cent by weight of mono- and diesters.

The present invention furthermore relates to a bath additive preparation, in particular an oil bath preparation, in which the advantageous actions of the polyglycerol fatty acid ester mixture according to the invention are particularly shown to advantage.

The bath additive preparation according to the invention, in particular an oil bath preparation, contains a polyglycerol fatty acid ester mixture of mono-, di- and polyesters of polyglycerols having a degree of polymerization of 2 to 8 and at least one saturated and/or unsaturated fatty acid, at least one oily or oil-containing component selected from the natural and synthetic, mineral, ethereal and fatty animal and vegetable oils, optionally a solvent or solvent mixture, and optionally further adjuvants and additives, and is characterized in that it comprises:

10 to 60 wt-% of a polyglycerol fatty acid ester mixture as a water-soluble emulsifier and/or solubilizer, 10 to 60 wt-% of an oil, oil mixture and/or oil component having cosmetic and/or therapeutic activity, and 0 to 70 wt-% of water, the polyglycerol fatty acid ester mixture (relative to 100 parts by weight of the polyglycerol fatty acid ester mixture) containing 20 to 65 wt-% of triglycerol fatty acid esters, 20 to 50 wt-% of tetraglycerol fatty acid esters, and 5 to 40 wt-% of higher polyglycerol fatty acid esters and containing no or only small amounts (less than 5 wt-%) of diglycerol fatty acid esters, and the fatty acid component consisting of one or more fatty acids selected from the saturated and/or unsaturated, branched and/or unbranched $C_6$- to $C_{14}$-fatty acids containing less than 10 wt-% of fatty acids having more than 14 carbon atoms.

The outstanding emulsifying and/or solubilizing action of the polyglycerol fatty acid ester mixture according to the invention preferably also proves very advantageous in bath additive preparations which contain oily or oil-containing substances which are naturally difficult to emulsify or solubilize. The excellent spontaneous emulsification power of the polyglycerol fatty acid ester mixture according to the invention is seen in particular when incorporating the bath additive preparation according to the invention into strongly diluted aqueous solutions, such as, for example, bath water, the oily or oil-containing component in, and/or on the surface of (spreading), the bath water being finely dispersed so that it can optimally achieve its cosmetic and/or therapeutic action.

The bath additive composition according to the invention is not only physiologically acceptable and readily biodegradable, but it also has a skin-caring and skin-protecting, particularly an oil-restoring, effect - which also leads on high dilution of the bath additive preparation according to the invention in bath water to a pleasant feel to the skin after the bath and counteracts the tendency of the bath water to dry out the skin.

Depending on the specific choice of the oil, oil mixture and/or oil component having a cosmetic and/or therapeutic effect, particular care properties and/or medicinal-therapeutic or pharmacological effects, such as, for example, healing, relieving, tranquilizing, relaxing, regenerating and/or vitalizing physiological actions, are incorporated in the bath additive preparation according to the invention.

According to one preferred embodiment, the bath additive composition according to the invention contains 15 to 50 wt-% of a polyglycerol fatty acid ester mixture, 15 to 50 wt-% of an oil, oil mixture and/or oil component having cosmetic and/or therapeutic activity, and 0.5 to 60 wt-% of water, the polyglycerol fatty acid ester mixture (relative to 100 parts by weight of the polyglycerol fatty acid ester mixture) containing 22 to 32 wt-% of triglycerol fatty acid esters, 39 to 49 wt-% of tetraglycerol fatty acid esters, and 24 to 34 wt-% of higher polyglycerol fatty acid esters, and containing no or only small amounts (less than 3 wt-%) of diglycerol fatty acid esters and the fatty acid component consisting of one or more fatty acids selected from the saturated and/or unsaturated, branched and/or unbranched $C_8$- to $C_{12}$-fatty acids containing less than 5 wt-% of fatty acids having more than 14 carbon atoms.

As the fatty acid component in the polyglycerol fatty acid ester mixture according to the invention, bath additive preparations according to the invention preferably contain caprylic acid, capric acid, lauric acid, undecenoic acid, 2-ethylhexanoic acid or coconut fatty acid. It is also possible for these fatty acids to be present as mixtures with one another. Additional or particular properties can be incorporated in the polyglycerol fatty acid ester mixture according to the invention by means of the aforementioned compounds. These include, for example, either advantageous skin-care properties or, as in the case of undecenoic acid, an antimycotic action, which is advantageous for preserving the bath additive preparation.

As an oil having a cosmetic effect, the bath additive preparation according to the invention preferably contains fatty vegetable oils, such as jojoba oil, soya oil, sesame oil, groundnut oil, sunflower oil, olive oil, palm oil, palm kernel oil, castor oil, cocoa oil, coconut oil, almond oil or wheatgerm oil. These oils may be employed individually or in mixtures with one another.

In addition, the bath additive preparation according to the invention may contain cosmetic animal oils, preferably synthetic uropygial gland oil, which increases the hydrophobicity of the skin and which can be incorporated in the bath additive preparation according to the invention without formation of precipitates due to the excellent solubilizing capacity of the polyglycerol fatty acid ester mixture according to the invention.

Particular pharmacological or medicinal-therapeutic properties are incorporated in the bath additive preparation according to the invention by using oils or oil mixtures having a corresponding medicinal or therapeutic action, preferably by addition of ethereal oils, such as rosemary oil, lavender oil, balm mint oil, sage oil, garlic oil, juniper berry oil, aniseed oil, cardamon oil, pimento oil, aniseed oil, caraway oil, lemon oil, orange oil, peppermint oil, camphor oil, clove oil, pine-needle oil or eucalyptus oil. These oils may be employed either individually or in mixtures with one another.

As the oil and/or oil component having a cosmetic effect, the bath additive preparation according to the invention can furthermore contain natural or synthetic compounds, such as, preferably, isopropyl myristate, isopropyl palmitate, decyl oleate, 2-octyldodecanol, cetyl stearyl isononanoate, lanolin or cholesterol derivatives and caprylic/capric acid triglyceride, it being possible for these compounds to be employed on their own or in mixtures with one another and also to have a skin-caring and/or oil-restoring action.

The aforementioned natural or synthetic, fatty vegetable and animal oils and also ethereal oils and oil components can be mutually completely or partially replaced in the bath additive preparation according to the invention. However, they can also be completely or partially replaced in the bath additive preparation according to the invention by pharmaceutical or therapeutic mineral oils or oil mixtures, such as, for example, liquid paraffin.

An additional perfuming effect can be incorporated in the bath additive preparation according to the invention by the addition of certain ethereal oils, preferably rose oil, jasmine oil, violet oil, mimosa oil, orange oil, neroli oil, patchouli oil, sandalwood oil or cinnamon oil and also by the addition of synthetic or natural perfume compositions, it being possible to employ these oils on their own or in mixtures with one another. A so-called scented bath is then obtained.

Solutions of vegetable extracts, such as those of camomile, can be contained in the bath additive preparation as further therapeutic substances in order, for example, to relieve or to heal inflammatory processes on the skin and in the respiratory tract organs.

The bath additive preparation according to the invention can also be formulated as a foam bath. To do this, foam-active agents are additionally incorporated, such as, for example, anionic surfactants, preferably alkyl ether sulfonates and sulfates, in particular sodium lauryl ether sulfate, in order to obtain a good foaming power even in the presence of significant amounts of oil or fat.

As a solvent, the bath additive preparation according to the invention can contain water, preferably demineralized water, which optionally contains small amounts of water-soluble organic solvents which are acceptable in health terms. These are, for example, glycerol and/or lower alcohols, such as 1,2-propanediol, which can be employed as additional solubilizers and prevent turbidity in the bath additive preparation by means of flocculation of organic constituents.

The use of small amounts of water as a solvent is particularly advantageous if the bath additive preparation of emulsifying or solubilizing polyglycerol fatty acid ester mixture according to the invention and the oily or oil-containing component forms a turbid solution. An optically clear solution is then obtained by the addition of water.

The polyglycerol fatty acid ester mixture according to the invention exhibits its superiority compared to commercially available products in particular with respect to its excellent solubilizing power in water-containing oil bath preparations.

The polyglycerol fatty acid ester mixture according to the invention can additionally be combined with a further polyglycerol fatty acid ester mixture as a solubilizer. Particularly suitable for this purpose is a polyglycerol caprate or a polyglycerol cocoate which are preferably prepared according to our own unpublished Patent Application P 41 05 305.2.

With a higher content of vegetable oils, in particular in a water-containing preparation, it may be advantageous to protect the bath additive preparation according to the invention from microbial decay. Compounds such as benzoates, benzoic acid derivatives, sorbates, microbiologically active phenols, such as 2,6-di-tert-butyl-methylphenol, and dioxanes, such as 5-bromo-5-nitro-1,3-dioxane, can be employed as bacteriostatic or bactericidal preservatives.

The bath additive preparation according to the invention can be provided with antioxidants, such as tocopherols, in particular vitamin E, and/or butylhydroxytoluene, against oxidative decomposition.

The preservatives are employed in the bath additive preparation according to the invention in customary amounts.

Further additives or auxiliaries which can be contained in the bath additive preparation according to the invention are pH regulators, thickeners or viscosity regulating agents, such as polyglycols, propylene glycol, ethanol, isopropanol, sodium polyacrylate and/or inorganic salts, preferably sodium chloride, complexing agents for masking metal ions, humectants, such as diglycerol, and colorants.

The bath additive preparation according to the invention displays its advantageous action in particular in an amount of from 15 to 30 ml to about 200 liters of bath water.

The bath additive preparation according to the invention is prepared by simple mixing of the constituents in appropriate mixing devices, the sequence of the addition of the individual components being arbitrary.

The present invention additionally relates to a process for the preparation of a polyglycerol fatty acid ester mixture of mono-, di- and polyesters of polyglycerols having a degree of polymerization of 2 to 8 and at least one saturated and/or unsaturated fatty acid, the process being characterized in that a polyglycerol which (relative to 100 parts by weight of polyglycerol) contains 20 to 65 wt-% of triglycerol, 20 to 50 wt-% of tetraglycerol and 5 to 40 wt-% of higher polyglycerols and contains no or only small amounts (less than 5 wt-%) of diglycerol, is reacted with one or more fatty acids, selected from the saturated and/or unsaturated, branched and/or unbranched $C_6$- to $C_{14}$-fatty acids, the fatty acid or the fatty acid mixture containing less than 10 wt-% of fatty acids having more than 14 carbon atoms, in a molar ratio of the polyglycerol to the fatty acid or to the fatty acid mixture of 4:1 to 1:1, preferably 2.5:1 to 1.5:1 in the presence of at least one catalyst, preferably an acidic catalyst, and at reduced pressure, by first heating the reaction mixture to 140° C., preferably 145° C., and reducing the pressure to 600 mbar, preferably 500 mbar, and then heating the reaction mixture in a temperature range from 140° to 220° C., preferably 145° to 190° C., stepwise or continuously, controlled by means of a temperature program, and at the same time reducing the pressure stepwise or continuously, controlled by means of a pressure program, from 600 to 10 mbar, preferably from 500 to 20 mbar, the resultant water of reaction being continuously removed by distillation and, upon attaining an acid number of <3, the resulting polyglycerol fatty acid ester mixture being cooled and optionally worked up and/or purified.

Particularly preferably, a molar ratio of the polyglycerol to the fatty acid or to the fatty acid mixture of 2:1 is set in the process according to the invention.

The process according to the invention allows the preparation of polyglycerol fatty acid ester mixtures of defined hydrophilicity by a simple and economical reaction procedure in which a constant quality and reproducible composition of the polyglycerol fatty acid ester mixture is guaranteed.

According to a preferred embodiment of the process according to the invention, a polyglycerol is employed which (relative to 100 parts by weight of polyglycerol) contains 22 to 32 wt-% of triglycerol, 39 to 49 wt-% of tetraglycerol and 24 to 34 wt-% of higher polyglycerols and contains no or only small amounts (less than 3 wt-%) of diglycerol.

As used herein the term "polyglycerol" refers generally to mixtures polyglycerols or glycerol oligomers of varying chain length.

The polyglycerol or polyglycerol mixture employed according to the invention is preferably prepared from the product mixture (polyglycerol) obtained according to German Patent No. DE 3,721,003 or according to Published German Application No. DE 3,410,520, by working up these polyglycerol mixtures by distillation, whereby diglycerol, in particular, is removed.

According to one preferred embodiment, a fatty acid or a fatty acid mixture, selected from the saturated and/or unsaturated, branched and/or unbranched $C_8$- to $C_2$-fatty acids containing less than 5 wt-% of fatty acids having more than 14 carbon atoms is employed in the process according to the invention.

According to a further preferred embodiment of the process according to the invention, the resulting polyglycerol fatty acid ester mixture is purified and/or worked up in order to at least partially remove unreacted polyglycerol from the product of the process; this being advantageous or necessary for certain applications.

To achieve this, the polyglycerol fatty acid ester mixture obtained by the process according to the invention is cooled to 30° to 110° C., preferably 60° to 80° C., and subsequently subjected to an extraction treatment by treating the polyglycerol fatty acid ester mixture with an organic chemical solvent or solvent mixture and then extracting polyglycerol with water, preferably in a single extraction step, an amount by weight of an inorganic and/or organic, basic compound corresponding to the acid number of the polyglycerol fatty acid ester mixture and/or at least equivalent to the amount of catalyst additionally being added in the first extraction step, and the organic phase remaining after the extraction being freed from the organic solvent employed and the residual water content by distillation, preferably vacuum distillation or vacuum evaporation.

The organic chemical solvent or solvent mixture employed in the extraction treatment desirably has a water absorption power of less than 30 wt-%, preferably less than 20 wt-% (relative to 100 parts by weight of the organic chemical solvent or solvent mixture), and/or forms an azeotropic mixture with water during the distillation or in the gas phase.

One organic chemical solvent which has these properties is ethyl acetate. If ethyl acetate is used in the extraction process, it is preferably employed as a water-saturated organic phase. Other organic chemical solvents which can be used according to the invention include, inter alia, butanol and/or toluene.

The neutralization of the catalyst is preferably carried out according to the invention using sodium hydroxide, in particular using aqueous sodium hydroxide solution, the alkaline compound or solution being added in the first extraction step to the organic chemical solvent or solvent mixture and/or to the water phase.

Other suitable neutralizing agents include alkali metal carbonates, preferably sodium carbonate and/or potassium carbonate, and/or a basic ion exchanger, which in each case are added to the organic chemical solvent or solvent mixture and/or to the water phase in the first extraction step.

If the polyglycerol fatty acid ester mixture prepared according to the invention is allowed to stand before further processing and/or purification for more than 0.5 hour, preferably 1 to 10 hours, unreacted contents of polyglycerol can optionally be precipitated and separated from the product mixture.

The constant quality of the final product, the defined composition of the ester mixture and the reproducibility of the reaction result are obtained in this process in particular by means of the controlled reaction sequence with respect to heating and simultaneous pressure reduction in the reaction mixture and also by the exact maintenance of specific pressure and temperature ranges.

The reaction sequence of the process according to the invention can be carried out continuously, controlled by means of an appropriate temperature and pressure program controller, or batchwise by means of stepwise heating and pressure reduction.

In this regard, it has been found to be advantageous to carry out the heating of the reaction mixture in the temperature range from 140° to 220° C., preferably 145° to 190° C., and to carry our the pressure reduction from 600 to 10 mbar, preferably from 500 to 20 mbar, in a time interval of from 2 to 6 hours, preferably 3 to 4 hours.

According to a further preferred embodiment of the process according to the invention, the heating of the reaction mixture in the temperature range from 140° to 220° C., preferably 145° to 190° C., is carried out stepwise in 3 to 6 steps, preferably 4 or 5 steps.

Corresponding to this, the reduction of the pressure from 600 to 10 mbar, preferably 500 to 20 mbar, can be performed stepwise in a specified number of steps, preferably in 3 to 6 steps, in particular 4 or 5 steps.

The esterification reaction in the process according to the invention is carried out in the presence of a catalyst, preferably in the presence of an acidic compound containing sulfonic acid groups, such as, for example, dodecylbenzenesulfonic acid or other alkyl-benzenesulfonic acids.

According to one embodiment, this acidic catalyst is employed in combination with a second acidic compound having catalytic and reducing action. A suitable compound in this respect is hypophosphorous acid.

According to a further advantageous embodiment of the process according to the invention, the reaction mixture is reacted in the presence of an inert gas, preferably nitrogen.

The invention furthermore relates to the use of the polyglycerol fatty acid ester mixture according to the invention as an emulsifier, solubilizing agent, dispersing agent, wetting agent and/or oil-restoring agent in cosmetic, pharmaceutical or chemicotechnical preparations.

The polyglycerol fatty acid ester mixture according to the invention has many uses. It is preferably used for the emulsification and/or dispersion and/or solubilization of natural or synthetic, ethereal, mineral, fatty animal or vegetable oils. It is particularly outstandingly suitable for preparing oil-containing bath additives, preferably bath oils or oil baths.

In addition, the polyglycerol fatty acid ester mixture according to the invention is used as a skin-care additive and/or detergent, cleaning agent or body shampoo, shower gel or shower composition, foam bath composition, liquid hand-cleaning agent or hair shampoo, since in addition to the surface-active property it also has a mild cleaning action as well as an oil-restoring effect and gives a pleasant feel to the skin during and after the cleaning process.

Other areas of use for the polyglycerol fatty acid ester mixture according to the invention are foodstuffs and medicaments, ointments, pharmaceutical and cosmetic preparations of any type where the polyglycerol fatty acid ester mixture acts as a solubilizing agent and/or emulsifier or dispersing agent and/or wetting agent. Its many uses result, inter alia, from the fact that, on the one hand, the polyglycerol fatty acid ester mixture according to the invention is easily processable, and on the other hand, it is neutral or beneficial to the skin and body. Cosmetic preparations using the polyglycerol fatty acid ester mixture according to the invention impart an optimum feeling of care. When used on the skin, e.g. in cosmetic preparations, skin disinfectants, ointments, embrocations and the like, the polyglycerol fatty acid ester mixture according to the invention has an oil-restoring action.

In addition, the polyglycerol fatty acid ester mixture according to the invention is especially suitable for industrial applications, preferably as an emulsifier in drilling oils or drilling fluids as well as lubricating oils, and also as a wetting and/or dispersing agent in industrial cleaning agents or as an emulsifier and/or dispersing agent in dye preparations, preferably in disperse dyes, or preservatives for buildings, in particular protective coatings and glazes for wood.

The polyglycerol fatty acid ester mixture according to the invention can additionally be employed as a water-soluble lubricant in chemicotechnical preparations.

The polyglycerol fatty acid ester mixture according to the invention can be combined without difficulty with other additives or adjuvants in ready-to-use formulations. Electrolytes and/or other surfactants and also solvents and/or diluents can preferably additionally be employed in detergents, cleaning agents and/or body shampoos. In addition, the polyglycerol fatty acid ester mixture according to the invention can be used together with preservatives, perfuming compositions, colorants, pharmaceutically active compounds, pH-adjusting compositions for pH regulation, complexing agents for masking metal ions, skin-care agents and/or thickening agents and other compounds such as colloids, active disinfectants, compounds having fungicidal, insecticidal and/or antibacterial activity, corrosion inhibitors, etc.

The following preparative examples and use examples are intended to illustrate the invention in further detail with out restricting its scope.

Example 1:

Preparation of polyglycerol caprate.

A mixture of 2608 g of polyglycerol (average molecular weight: about 326 g/mole; consisting of about 30% triglycerol, about 45% tetraglycerol, about 17% pentaglycerol, and about 8% higher oligomers), 688 g=4 moles of capric acid, 5.6 g of dodecylbenzenesulfonic acid and 2.2 g of hypophosphorous acid was heated up to a maximum of 155° C. at 400 to 40 mbar during the course of about 3 h with stirring and simultaneous passage of inert gas in a 4-liter four-neck flask which was provided with a stirrer, water separator, thermometer and gas inlet tube, the water of reaction being continuously removed by distillation. On attaining an acid number of <2, the reaction mixture was cooled down to about 65° C. and unreacted contents of polyglycerol were removed as follows:

The reaction mixture was dissolved in ethyl acetate (half the amount by volume) and extracted with water. The amount of sodium hydroxide solution corresponding to the acid number was added to the water. The amount of water used for extraction was about 50% by volume of the ester employed. The total of the extracted contents of polyglycerol after removal of the solvent by distillation was about 20 wt-% of the crude ester employed. The organic phase remaining after the extraction was evaporated in vacuo (residual content of water: 10 wt-%).
Characterizing data:
  Acid number: <2
  Hydrolysis number: 75–85
  HLB: 14.3

Example 2:

Preparation of polyglycerol laurate.

A mixture of 886 g of polyglycerol (average molecular weight: about 326 g/mole; consisting of about 30% triglycerol, about 45% tetraglycerol, about 17% pentaglycerol, and about 8% higher oligomers), 272 g=1.36 moles of lauric acid, 2.8 g of dodecylbenzenesulfonic acid and 1.1 g of hypophosphorous acid was heated up to a maximum of 155° C. at 400 to 40 mbar during the course of about 3 hours with stirring and simultaneous passage of inert gas in a 2-liter four-neck flask which was provided with a stirrer, water separator, thermometer and gas inlet tube, the water of reaction being continuously removed by distillation. On attaining an acid number of <2, the reaction mixture was cooled down to about 70° C. and unreacted contents of polyglycerol were removed as follows:

The reaction mixture was dissolved in ethyl acetate (half the amount by volume) and extracted with water. The amount of sodium hydroxide solution corresponding to the acid number was added to the water. The amount of water used for extraction was about 50% by volume of the ester employed. The total of the extracted contents of polyglycerol after removal of the solvent by distillation was about 31 wt-% of the crude ester employed. The organic phase remaining after the extraction was evaporated in vacuo.
Characterizing data:
  Acid number: 0.9
  Hydrolysis number: 98.4
  HLB: 13.0

Example 3:

Preparation of polyglycerol caprylcaprate.

A mixture of 2457 g of polyglycerol (average molecular weight: about 273 g/mole; consisting of about 4% diglycerol, about 62% triglycerol, about 24% tetraglycerol, about 7% pentaglycerol, and about 3% higher oligomers), 706 g=4.5 moles of caprylic/capric acid mixture, 6.3 g of dodecylbenzenesulfonic acid and 2.5 g of hypophosphorous acid was heated up to a maximum of 155° C. at 400 to 40 mbar during the course of about 3 hours with stirring and simultaneous passage of inert gas in a 4-liter four-neck flask which was provided with a stirrer, water separator, thermometer and gas inlet tube, the water of reaction being continuously removed by distillation. Upon attaining an acid number of <2, the reaction mixture was cooled down to about 70° C., and unreacted polyglycerol was removed as follows:

The reaction mixture was dissolved in ethyl acetate (half the amount by volume) and extracted with water. An amount of sodium hydroxide solution corresponding to the acid number was added to the water. The amount of water used for extraction was about 50% by volume of the ester employed. The total amount of extracted polyglycerol after removal of the solvent by distillation was about 25 wt-% of the crude ester employed. The organic phase remaining after the extraction was evaporated in vacuo.
Characterizing Data:
  Acid number: 1.0
  Hydrolysis number:. 108.9
  HLB: 12.3

Examples of use of Polyglycerol Fatty Acid ester mixtures prepared according to the invention Example I Oil/water body lotion containing polyglycerol laurate of the invention as an oil/water emulsifier.

A composition was prepared comprising the following ingredients:

1.5 wt-% polyglycerol laurate according to the invention (Prepn. Example 2)

0.5 wt-% sodium polyacrylate 5.0 wt-% liquid paraffin, viscous, GB 4.0 wt-% acetylated lanolin 6.0 wt-% cetyl stearyl isononanoate 4.0 wt-% diglycerol 0.05 wt-% preservative 0.3 wt-% perfume 78.65 wt-% water (completely demineralized)

The product was a white, stable emulsion with very good absorption power and outstanding feel to the skin.

Centrifuge test 20 min. 5000 rpm: no separation Viscosity, measured with Haake viscometer, VT 181, MV DIN/32 at 20° C.: 3500 mPa.s

Example II

Oil/water body lotion containing natural or identical-to-natural raw materials and the polyglycerol laurate of the invention as an oil/water emulsifier.

A composition was prepared comprising the following ingredients:

2.0 wt-% polyglycerol laurate according to the invention (Prepn. Example 2)

0.5 wt-% sodium polyacrylate 6.0 wt-% wheatgerm oil 6.0 wt-% cetyl stearyl isooctanoate (synthetic uropygial gland oil)

7.0 wt-% caprylic/capric acid triglyceride 4.0 wt-% diglycerol 0.05 wt-% preservative 0.3 wt-% perfume 74.15 wt-% water (completely demineralized)

The product was a slightly yellow, lustrous, stable emulsion.

Centrifuge test, 20 min. @ 5000 rpm: no separation viscosity measured using Haake viscometer VT 181, MV DIN/32 at 20° C.: 3000 mPa.s

Example III

Rosemary bath oil.

A composition was prepared comprising the following ingredients:

27 wt-% rosemary oil 33 wt-% polyglycerol caprate according to the invention (Prepn. Example 1)

40 wt-% water (completely demineralized)

The product was a clear, low-viscosity oil having good emulsifying power in warm water and good oil-restoring capacity on the skin.

Example IV

Pine-needle bath oil.

A composition was prepared comprising the following ingredients:

20 wt-% pine-needle oil 45 wt-% polyglycerol caprylcaprate according to the invention (Prepn. Example 3)

35 wt-% water (completely demineralized)

The product was a clear, low-viscosity oil having good emulsifying power in warm water and good oil-restoring capacity on the skin.

Example V

Rosemary bath oil containing water.

A composition was prepared comprising the following ingredients:

20 wt-% rosemary oil 50 wt-% polyglycerol caprate according to the invention (Prepn. Example 1)

30 wt-% water (completely demineralized)

The product was a clear, low-viscosity oil having good emulsifying power in warm water and good oil-restoring capacity on the skin.

Example VI

Spreading oil bath preparation having high skin-care action.

A composition was prepared comprising the following ingredients:

20 wt-% polyglycerol caprate according to the invention (Prepn. Example 1)

20 wt-% polyglycerol caprate (Prepn. DE 4,105,305.2)

20 wt-% isopropyl myristate 31 wt-% liquid paraffin GP, viscous 5 wt-% perfume oil 4 wt-% water (completely demineralized)

Example VII

Spontaneously emulsifying bath oil with skin-care properties.

A composition was prepared comprising the following ingredients:

25 wt-% polyglycerol caprate according to the invention (Prepn. Example 1)

17 wt-% polyglycerol cocoate (Prepn. DE 4,105,305.2)

33 wt-% isopropyl myristate 20 wt-% jojoba oil 5 wt-% perfume oil.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A polyglycerol fatty acid ester mixture of mono-, di- and polyesters of a polyglycerol having a degree of polymerization of 2 to 8 and at least one fatty acid selected from the group consisting of saturated and unsaturated, branched and unbranched $C_6$- to $C_{14}$-fatty acids containing less than 10 wt-% of fatty acids having more than 14 carbon atoms, wherein said polyglycerol fatty acid ester mixture has an HLB of greater than 8 and contains 0 to 5 parts by weight diglycerol fatty acid esters, 20 to 65 parts by weight triglycerol fatty acid esters, 20 to 50 parts by weight tetraglycerol fatty acid esters, and 5 to 40 parts by weight higher polyglycerol fatty acid esters, in a total of 100 parts by weight of said ester mixture.

2. A polyglycerol fatty acid ester mixture according to claim 1, having an HLB of greater than 10 and containing 0 to 3 parts by weight of diglycerol fatty acid esters, 22 to 32 parts by weight of triglycerol fatty acid esters, 39 to 49 parts by weight tetraglycerol fatty acid esters, and 24 to 34 parts by weight higher polyglycerol fatty acid esters, in a total of 100 parts by weight of said mixture, and wherein the fatty acid consists of at least one fatty acid selected from the group consisting of saturated and unsaturated, branched and unbranched $C_8$- to $C_{12}$-fatty acids containing less than 5 wt-% of fatty acids having more than 14 carbon atoms.

3. A polyglycerol fatty acid ester mixture according to claim 1, containing 5 to 20 wt-% pentaglycerol fatty acid esters.

4. A polyglycerol fatty acid ester mixture according to claim 1, in which the fatty acid consists of at least one fatty acid selected from the group consisting of caprylic acid, capric acid, lauric acid, undecenoic acid, 2-ethylhexanoic acid and coconut fatty acid.

5. A polyglycerol fatty acid ester mixture according to claim 1, containing more than 50 wt-% monoesters and diesters.

6. A bath additive composition comprising:

10 to 60 wt-% of a polyglycerol fatty acid ester mixture of mono-, di- and polyesters of a polyglycerol having a degree of polymerization from 2 to 8 and at least one fatty acid selected from group consisting of saturated and unsaturated, branched and unbranched $C_6$- to $C_{14}$-fatty acids containing less than 10 wt-% of fatty acids having more than 14 carbon atoms;

10 to 60 wt-% of at least one oil or oil-component having cosmetic or therapeutic activity selected from the group consisting of natural and synthetic, mineral, ethereal and fatty animal and vegetable oils, and 0 to 70 wt-% water;

wherein said polyglycerol fatty acid ester mixture has an HLB of greater than 8 and contains 0 to 5 parts by weight diglycerol fatty acid esters, 20 to 65 parts by weight triglycerol fatty acid esters, 20 to 50 parts by weight tetraglycerol fatty acid esters, and 5 to 40 parts by weight higher polyglycerol fatty acid esters, in a total of 100 parts by weight of said ester mixture.

7. A composition according to claim 6, further comprising at least one solvent.

8. A composition according to claim 6, which is an oil bath composition.

9. A composition according to claim 6, comprising:

15 to 50 wt-% polyglycerol fatty acid ester mixture in which the fatty acid consists of at least one fatty acid selected from the group consisting of saturated and unsaturated, branched and unbranched $C_8$- to $C_{12}$-fatty acids containing less than 5 wt-% of fatty acids having more than 14 carbon atoms, 15 to 50 wt-% oil or oil component having cosmetic or therapeutic activity, and 0.5 to 60 wt-% water, wherein said polyglycerol fatty acid ester mixture contains 0 to 3 parts by weight diglycerol fatty acid esters, 22 to 32 parts by weight triglycerol fatty acid esters, 39 to 49 parts by weight tetraglycerol fatty acid esters, and 24 to 34 parts by weight higher polyglycerol fatty acid esters, in a total of 100 parts by weight of said ester mixture.

10. A process for preparing a polyglycerol fatty acid ester mixture of mono-, di- and polyesters of polyglycerols having a degree of polymerization of 2 to 8 and at least one saturated and/or unsaturated fatty acid, said process comprising the steps of initially heating a reaction mixture comprising a polyglycerol containing 0 to 5 wt-% diglycerol, 20 to 65 wt-% triglycerol, 20 to 50 wt-% tetraglycerol, and 5 to 40 wt-% higher polyglycerols, and at least one fatty acid selected from the group consisting of saturated and unsaturated, branched and unbranched $C_6$- to $C_{14}$-fatty acids containing less than 10 wt-% fatty acids having more than 14 carbon atoms, in a molar ratio of polyglycerol to fatty acid of 4:1 to 1:1 and in the presence of at least one catalyst, to a temperature of at least 140° C. and reducing the pressure to at most 600 mbar;

subsequently heating the reaction mixture in a temperature range from 140° to 220° C. under control of a temperature program, and simultaneously reducing the pressure under control of a pressure program from 600 to 10 mbar;

removing resulting water of reaction by continuous distillation, and upon attaining an acid number of less than 3, cooling the resulting polyglycerol fatty acid ester mixture.

11. A process according to claim 10, wherein said polyglycerol and said fatty acid are reacted in a molar ratio of 2.5:1 to 1.5:1.

12. A process according to claim 10, wherein said subsequent heating and pressure reduction are effected in steps.

13. A process according to claim 10 wherein said subsequent heating and pressure reduction are effected continuously.

14. A process according to claim 10, further comprising purifying the cooled polyglycerol fatty acid ester mixture.

15. A process according to claim 10, wherein said mixture is initially heated to 145° C. and the pressure is initially reduced to 500 mbar, and subsequently the mixture is heated to a temperature of from 145° to 190° C. and the pressure is simultaneously reduced to from 500 to 20 mbar.

16. A process according to claim 10, wherein said catalyst is an acidic catalyst.

17. A process according to claim 10, wherein said polyglycerol contains:

0 to 3 wt-% diglycerol, 22 to 32 wt-% triglycerol, 39 to 49 wt-% tetraglycerol, and 24 to 34 wt-% higher polyglycerols.

18. A process according to claim 10, wherein said at least one fatty acid is selected from the group consisting of saturated and unsaturated, branched and unbranched $C_8$- to $C_{12}$-fatty acids containing less than 5 wt-% of fatty acids having more than 14 carbon atoms.

19. A process according to claim 10, wherein the resulting polyglycerol fatty acid ester mixture is cooled to a temperature in the range from 30° to 110° C.; said process further comprising the steps of:

treating the cooled polyglycerol fatty acid ester mixture with an organic solvent or solvent mixture;

extracting the solvent-treated mixture with water in at least one extracting step to remove any unreacted polyglycerol and obtain an organic phase, and freeing said organic phase from organic solvent and residual water by distillation;

wherein an amount of a basic compound at least equivalent to the amount of catalyst used is added to the organic solvent or to the water in a first of said at least one extracting step.

20. A process according to claim 19, wherein said resulting polyglycerol fatty acid ester mixture is cooled to a temperature in the range from 60° to 80° C., the extracting is carried out in a single extraction step, and the organic phase is freed of organic solvent and residual water by vacuum distillation or vacuum evaporation.

21. A process according to claim 19, wherein an amount of basic compound at least equivalent to the acid number of the polyglycerol fatty acid ester mixture is added to the water used in said first extracting step.

22. A process according to claim 20, wherein said organic solvent or solvent mixture has a water absorption capacity of less than 30 wt-%.

23. A process according to claim 22, wherein said organic solvent or solvent mixture has a water absorption capacity of less than 20 wt-%.

24. A process according to claim 20, wherein said organic solvent or solvent mixture forms an azeotropic mixture with water during the distillation.

25. A process according to claim 20, wherein said organic solvent is ethyl acetate.

26. A process according to claim 25, wherein said organic solvent is ethyl acetate saturated with water.

27. A process according to claim 19, wherein said basic compound comprises sodium hydroxide.

28. A process according to claim 27, wherein said sodium hydroxide is in the form of an aqueous sodium hydroxide solution.

29. A process according to claim 19, wherein said basic compound comprises at least one basic substance selected from the group consisting of alkali metal carbonates and basic ion exchangers.

30. A process according to claim 29, wherein said basic compound comprises sodium carbonate or potassium carbonate.

31. A process according to claim 10, further comprising allowing said cooled polyglycerol fatty acid ester mixture to stand for at least about one-half hour, and separating any precipitated polyglycerols.

32. A process according to claim 31, wherein said cooled polyglycerol fatty acid ester mixture is allowed to stand for from 1 to 10 hours.

33. A process according to claim 10, wherein the step of subsequently heating the reaction mixture in a temperature range from 140° to 220° C. under control of a temperature program, and simultaneously reducing the pressure under control of a pressure program from 600 to 10 mbar is carried out in a time interval of from 2 to 6 hours.

34. A process according to claim 15, wherein the step of subsequently heating the reaction mixture in a temperature range from 145° to 190° C. and simultaneously reducing the pressure from 500 to 20 mbar is carried out in a time interval of from 3 to 4 hours.

35. A process according to claim 10, wherein said step of subsequently heating the reaction mixture in a temperature range from 140° to 220° C. under control of a temperature program is carried out stepwise in from 3 to 6 steps.

36. A process according to claim 15, wherein said step of subsequently heating the reaction mixture in a temperature range from 145° to 190° C. is carried out stepwise in 4 or 5 steps.

37. A process according to claim 10, wherein said step of reducing the pressure from 600 to 10 mbar is carried out stepwise in from 3 to 6 steps.

38. A process according to claim 15, wherein said step of reducing the pressure from 500 to 20 mbar is carried out stepwise in 4 or 5 steps.

39. A process according to claim 16, wherein said acidic catalyst is employed in combination with an acidic reducing compound.

40. A process according to claim 39, wherein said acidic catalyst is a compound containing at least one sulfonic acid group, and said acidic reducing compound is hypophosphorous acid.

41. A process according to claim 10, wherein said reaction mixture is heated under an inert gas atmosphere.

42. A process according to claim 41, wherein said reaction mixture is heated under a nitrogen atmosphere.

* * * * *